United States Patent

Propp et al.

[11] Patent Number: 5,975,897
[45] Date of Patent: Nov. 2, 1999

[54] ORAL SUCTIONING SWAB

[75] Inventors: Donald J. Propp, Dewitt; Gary A. Gillis, Rockford, both of Mich.

[73] Assignee: Tri-State Hospital Supply Corporation, Howell, Mich.

[21] Appl. No.: 09/201,040

[22] Filed: Nov. 30, 1998

[51] Int. Cl.⁶ .................................................. A61C 17/06
[52] U.S. Cl. ................ 433/91; 433/95; 604/902
[58] Field of Search .................. 433/91, 93, 94, 433/95, 96; 604/118, 119, 902

[56] References Cited

U.S. PATENT DOCUMENTS

| | | | |
|---|---|---|---|
| D. 269,811 | 7/1983 | Kaufman | D24/34 |
| D. 282,698 | 2/1986 | Newton, Jr. | D4/104 |
| D. 332,658 | 1/1993 | Thompson | D24/117 |
| 1,417,379 | 5/1922 | Horvin | 433/91 X |
| 1,447,020 | 2/1923 | Grunberg | 433/91 |
| 3,324,855 | 6/1967 | Heimlich | 128/269 |
| 4,158,916 | 6/1979 | Adler | 32/33 |
| 4,233,025 | 11/1980 | Larson et al. | 433/136 |
| 4,401,130 | 8/1983 | Halford et al. | 132/88.5 |
| 4,878,900 | 11/1989 | Sundt | 433/91 X |
| 4,935,001 | 6/1990 | George | 604/1 |
| 5,085,633 | 2/1992 | Hanifl et al. | 604/35 |
| 5,094,616 | 3/1992 | Levenson | 433/93 |
| 5,151,094 | 9/1992 | Hanifl | 604/902 |
| 5,203,699 | 4/1993 | McGuire | 433/93 |
| 5,230,626 | 7/1993 | Larson et al. | 433/91 X |
| 5,378,226 | 1/1995 | Hanifl et al. | 604/3 |

*Primary Examiner*—Nicholas D. Lucchesi
*Attorney, Agent, or Firm*—Fildes & Outland, P.C.

[57] ABSTRACT

An oral suctioning swab includes a rigid plastic tube of an elongated shape having first and second ends and a bend therebetween. A suctioning thumb control is bonded to the tube first end and a soft resilient tubular tip is bonded to said tube second end. A foam sleeve is bonded over the tube second end and soft resilient tubular tip such that the soft resilient tubular tip extends beyond the foam sleeve thereby avoiding any radial aspiration through the foam sleeve.

11 Claims, 3 Drawing Sheets

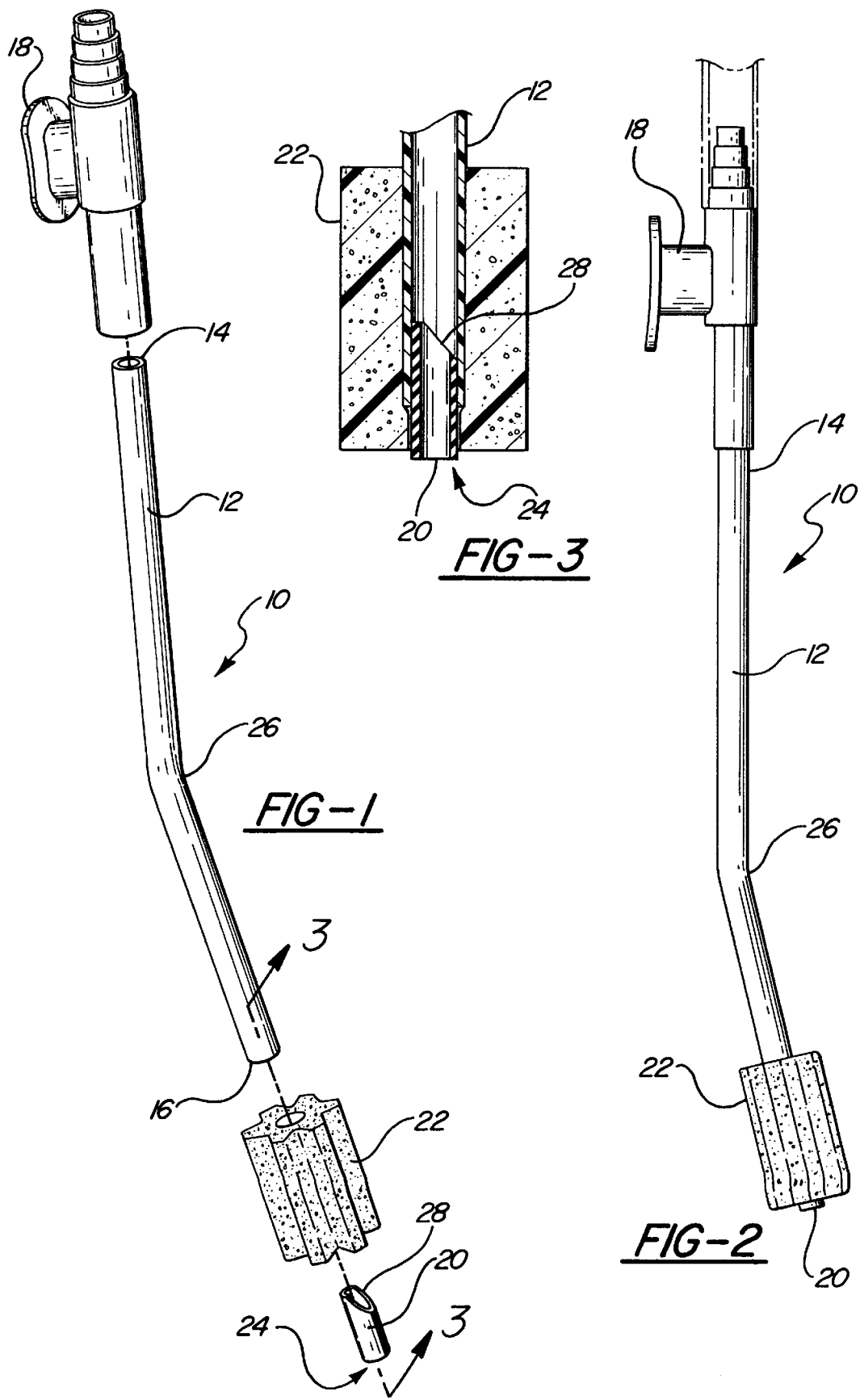

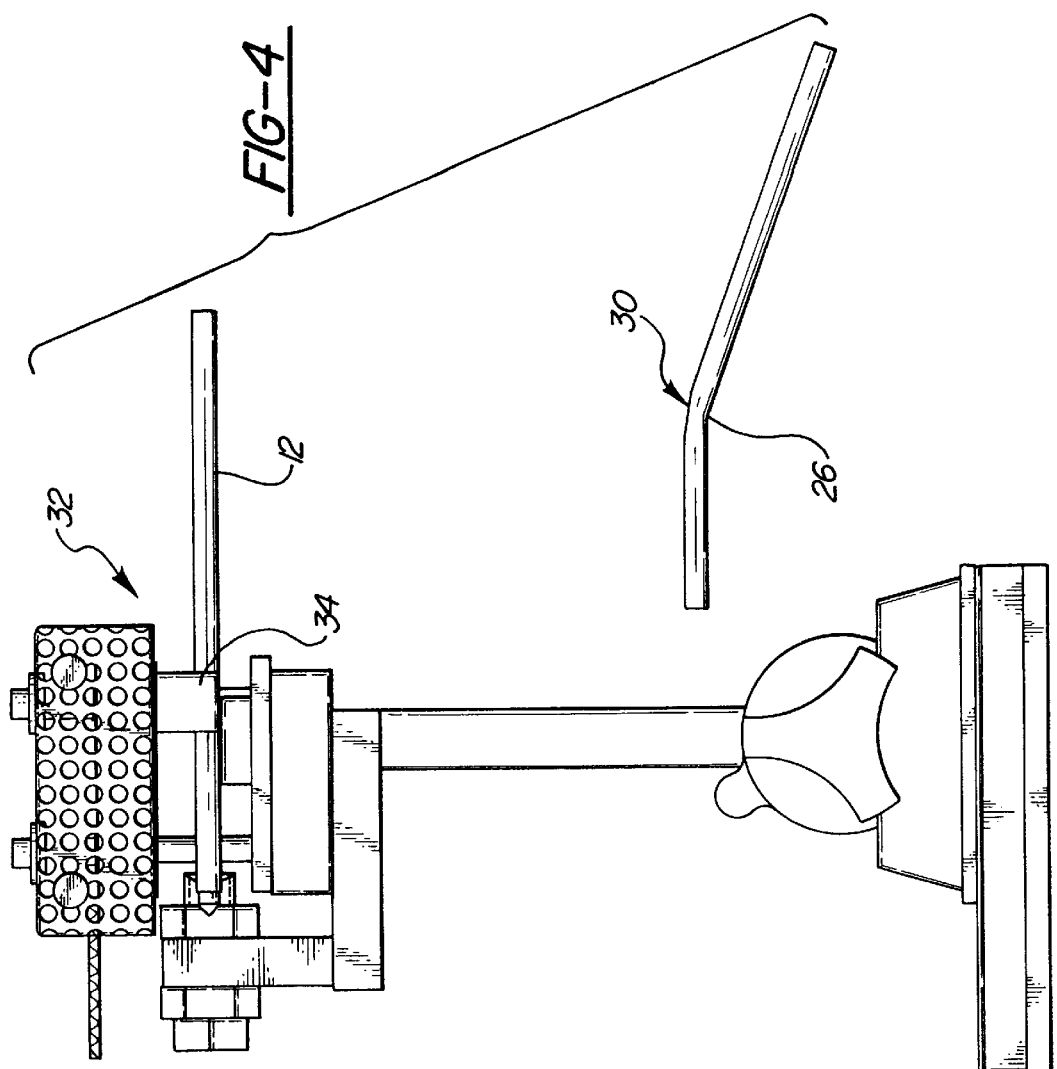
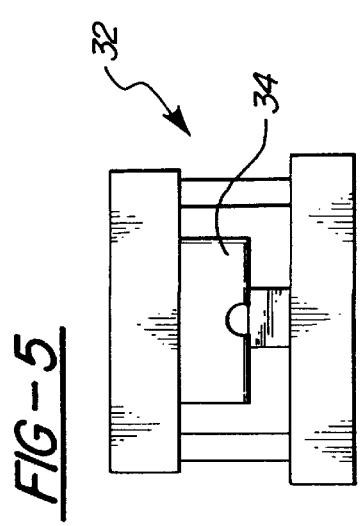

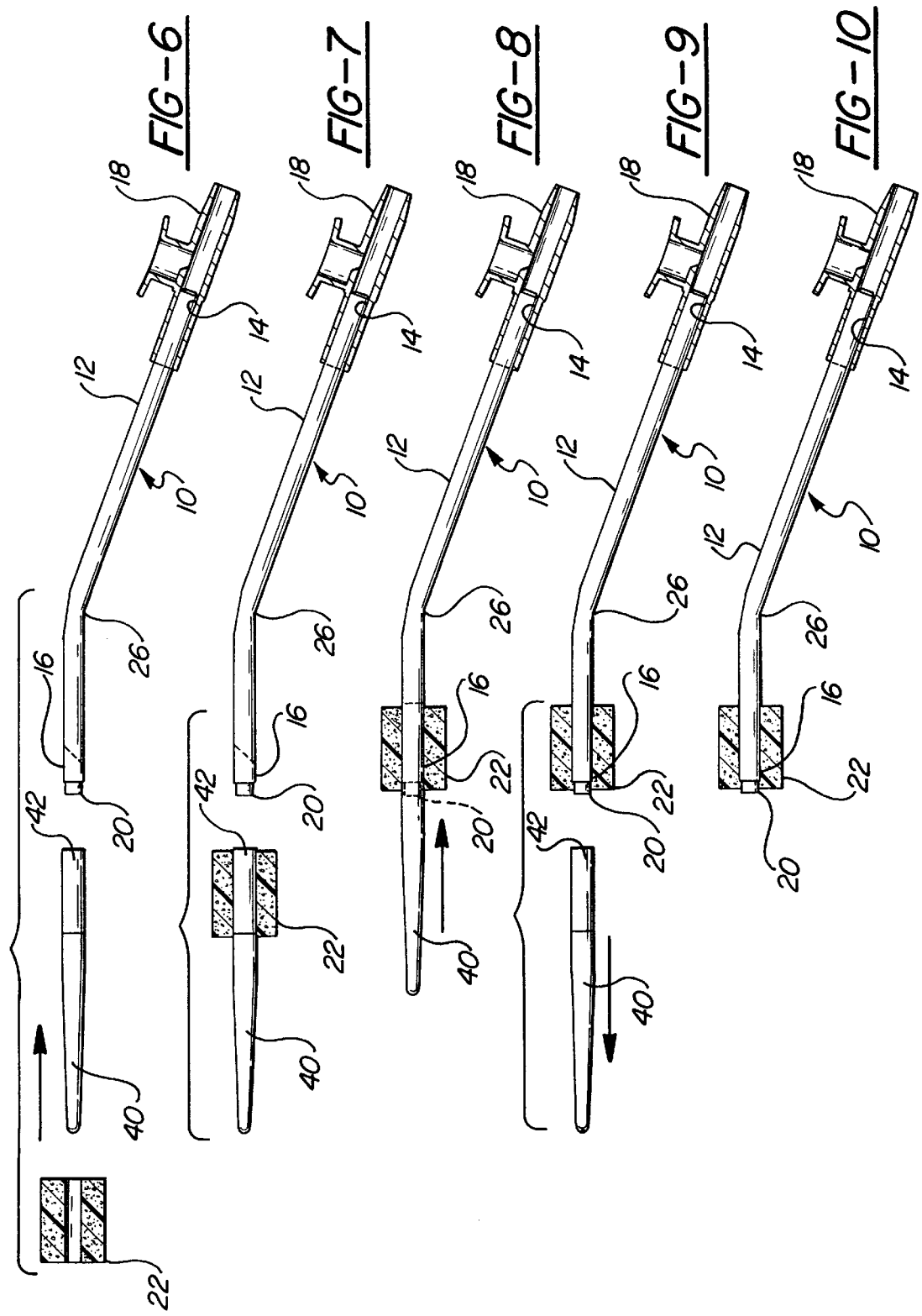

ORAL SUCTIONING SWAB

FIELD OF THE INVENTION

This invention relates to an oral suctioning swab for aspirating liquid and other material from the mouth of a patient.

BACKGROUND OF THE INVENTION

It is known in the art relating to oral swabs to apply vacuum force through a porous foam sleeve or through an aperture in the foam sleeve to remove liquid and other material from the mouth of a patient. Such oral swabs clog as the porous surface of the foam sleeve becomes filled or as the aperture in the foam sleeve becomes restricted with debris.

In addition, such oral swabs preclude removal of viscus fluid and/or material from oral recesses and recesses between the teeth and gum line. Often times the vacuum force drawn through the foam sleeve collapses the foam into the device and/or onto itself and causes the swab to fail to continue suctioning. Such side hole devices are difficult to manufacture as the foam sleeve must be properly placed on a vacuum supply tube end to ensure flow through the element. In some cases, an aperture in the foam sleeve must be aligned relative to an aperture in the vacuum supply tube end.

SUMMARY OF THE INVENTION

The present invention provides an oral suctioning swab that has a soft tip section extending beyond a foam sleeve which avoids the possibility of the foam sleeve collapsing or becoming clogged and is useful for massaging a patients gums.

The present invention also provides an oral suctioning swab that is able to remove debris from oral recesses and recesses between the teeth and gum line.

The present invention also provides a method of assembling an oral swab that simplifies the mounting of a foam sleeve on an aspirating tube, while assuring a reliable bond between the foam sleeve and aspirating tube.

More particularly, the oral suctioning swab of the invention comprises a rigid plastic tube of an elongated shape having first and second ends. A suctioning thumb control means is bonded to the tube first end and a soft resilient tubular tip is bonded to the tube second end. A foam sleeve is bonded over the tube second end and tubular tip such that the tubular tip extends beyond the foam sleeve thereby avoiding any aspiration through the foam sleeve.

In one embodiment of the invention the resilient tubular tip extends beyond the foam sleeve in the range of 1/16 and 3/16 inch whereby the foam sleeve cannot become clogged and/or collapse under the vacuum pressure.

Preferably, the rigid plastic tube is transparent to allow a caretaker to see that debris are actually being picked up. Also, the rigid plastic tube includes a bend of an obtuse angle between the foam sleeve and suctioning thumb means that facilitates following the natural anatomy and contours of the oral cavity.

In a preferred embodiment, the resilient tubular tip distal end includes radiused wall ends to facilitate gentle contact with a patient's gums without trauma.

A method of assembling the oral suctioning swab from the rigid plastic tube, suctioning thumb control, soft resilient tubular tip, and foam sleeve; comprises the steps of:

heating the rigid plastic tube by applying heat to one side of the rigid plastic tube, generally one-half the circumference of the tube;

bending the heated plastic tube to impart a bend in the plastic tube by bending the heated tube to the bent shape;

mounting a suctioning thumb control on one end of the bent tube by applying solvent on one end of the rigid plastic tube and sliding the thumb control over the tube end and solvent;

mounting the soft tip on the other end of the rigid plastic tube by applying solvent onto the soft tip and inserting the soft tip into the rigid plastic tube; and mounting the foam sleeve on a solvent coated rigid plastic tube and soft tip without relative sliding friction motion therebetween, such that the foam sleeve drops onto the rigid plastic tube, whereby the foam sleeve does not wipe the solvent off the bond surface area of the tube as it is moved onto the tube, and the soft tip extends beyond the foam sleeve.

In one embodiment, mounting the foam sleeve on the rigid plastic tube and soft tip without relative sliding friction motion therebetween includes the steps of:

mounting the foam sleeve on a tapered mandrel having a hollow center;

inserting the soft tip end of the tube into the hollow center of the mandrel;

restraining the foam sleeve from moving relative to the rigid plastic tube; and extracting the mandrel from the foam sleeve whereby the foam sleeve is dropped onto the solvent laden soft tip end and the rigid plastic tube without relative sliding friction motion between the foam sleeve and the soft tip and rigid plastic tube.

These and other features and advantages of the invention will be more fully understood from the following detailed description of the invention taken together with the accompanying drawings.

BRIEF DESCRIPTION OF THE DRAWINGS

In the drawings:

FIG. 1 is an exploded view of an oral suctioning swab constructed in accordance with the present invention;

FIG. 2 is an assembled view of the oral suctioning swab of FIG. 1;

FIG. 3 is a sectional view taken along lines 3—3 in FIG. 1;

FIG. 4 is a schematic view of a bending fixture and tube illustrating heated bending of the tube;

FIG. 5 is a schematic view of the bending fixture in FIG. 4 illustrating a heating tool for differential heating; and FIGS. 6 through 10 are sequential schematic views illustrating an assembly method of foam sleeve to rigid plastic tube and soft tip at one end of the oral suctioning swab.

DETAILED DESCRIPTION OF THE INVENTION

Referring now to the drawings in detail, numeral 10 generally indicates an oral suctioning swab for aspirating within the mouth of a patient. As is hereinafter more fully described, oral suctioning swab 10 can aspirate at the very back of the mouth in the corner of the gum and cheek to remove phlegm, mucus, and foodstuff.

FIGS. 1–3 illustrate one embodiment of an oral suctioning swab 10 having a transparent rigid plastic tube 12 of an elongated shape. Tube 12 has first and second ends 14,16. A suctioning thumb control 18 is bonded to the tube first end 14 and a soft resilient tubular tip 20 is bonded to the tube second end 16. A foam sleeve 22 is bonded over the tube second end 16 and tubular tip 20 such that the tubular tip extends beyond the foam sleeve thereby avoiding any radial aspiration through the foam sleeve.

In the illustrated embodiment, the resilient tubular tip 20 extends beyond the foam sleeve 22 in the range of 1/16 and 3/16 inch. The resilient tubular tip 20 is extended beyond the foam sleeve 22 to eliminate the possibility of the foam sleeve getting sucked into and stuck in the tube 12 by vacuum induced air and fluid flow current, or by being pushed against the tip end opening 24 during routine manipulation in the oral cavity. This construction also increases the bonding length of the foam sleeve 22 to the tube 12 and tip 20 resulting in a safer swab in which the foam sleeve will not come loose and potentially choke a patient.

The rigid plastic tube 12 illustrated in FIGS. 1 and 2 is transparent allowing a caretaker to see that debris is actually being picked up and moved out of the mouth during suctioning. The removal of blood, sloughed material, mouth rinse, mucus and foodstuffs are immediately observable.

Also, the rigid plastic tube 12 includes a bend 26 of an obtuse angle between the foam sleeve 22 and suctioning thumb control 18 near the foam sleeve that follows the natural anatomy and contours of the oral cavity. Bend 26 provides easy non-traumatic access without excessively stretching the patient's mouth and lips. Bend 26 also reduces any extra nurse contortions and effort traditionally associated with using swabs of straight geometry.

Referring to FIG. 3, the resilient tubular tip distal end 28 includes radiused wall ends allowing the tip to gently contact a patient's gums without trauma. End 28 allows total and complete removal of all debris/fluid from oral recesses and from recesses between the teeth and gum line. Aspiration at the end 28 and through opening 24 provides for easy removal of particles in pockets and crevices without pushing foodstuff and other debris into hard to reach areas. Soft plastic tip 20 can be used to massage the gums or to loosen or remove or jog necrotic tissue.

Referring now to FIGS. 4–9 of the drawings, a method of assembling the oral suctioning swab 10 includes the steps of heating the rigid plastic tube 12 by applying heat to one portion 30 of the rigid plastic tube, generally one-half the circumference of the tube. Heat is applied using a heated bending fixture 32 having a heat applying bending die 34 such as is illustrated in FIGS. 4 and 5. Applying heat around the circumference of the tube 12 only causes the tube to collapse or not retain the bent angle without further fixturing or manipulation. But applying heat only to about half the circumference and setting up a temperature differential prevents the tube 12 from collapsing or requiring further processing and allows it to immediately retain its bent shape.

As illustrated in FIG. 4, the tube 12 is placed in proper position in the heated bending die 34, heated and bent to impart a bend in the plastic tube. After bending, the tube 12 is removed and the desired bent shape is maintained until the plastic tube is sufficiently cool to freeze the shape therein.

With continuing reference to FIGS. 4 and 5 and with reference to FIGS. 6–10, the suctioning thumb control 18 is bonded on the first end 14 of the bent tube by applying solvent on the end of the rigid plastic tube and sliding the thumb control over the tube end and solvent. The soft tip 20 is bonded on the second end 16 of the tube 12 by applying solvent on the soft tip and inserting the soft tip into the rigid plastic tube. The foam sleeve 22 is then bonded on the rigid plastic tube 12 and soft tip 20 without relative sliding friction motion therebetween as hereinafter described, whereby no solvent is removed from the bonding area and the soft tip extends beyond the foam sleeve.

Referring to FIGS. 6–10, the foam sleeve 22 is mounted on a tapered mandrel 40 having a hollow center 42, expanding the inside diameter of the foam sleeve. The soft tip 20 and second tube end 16 after being wetted with solvent are inserted into the hollow center 42 of the mandrel 40. The foam sleeve 22 is restrained from moving relative to the rigid plastic tube and the mandrel 40 is then extracted from the foam sleeve 22 whereby the foam sleeve is dropped onto the tube second end 16 and soft tip 20 without wiping the solvent from the bonding area.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. An oral suctioning swab comprising:
   a rigid plastic tube of an elongated shape having first and second ends;
   a suctioning thumb control means bonded to said tube first end;
   a soft resilient tubular tip bonded to said tube second end; and
   a foam sleeve bonded over said tube second end and said tubular tip; said tubular tip extending beyond said foam sleeve.

2. The oral suctioning swab of claim 1 wherein said resilient tubular tip extends beyond said foam sleeve in the range of 1/16 and 3/16 inch.

3. The oral suctioning swab of claim 1 wherein said rigid plastic tube is transparent.

4. The oral suctioning swab of claim 1 wherein said rigid plastic tube includes a bend of an obtuse angle between said foam sleeve and suctioning thumb means.

5. The oral suctioning swab of claim 1 wherein said resilient tubular tip distal end includes radiused wall ends.

6. A method of assembling an oral suctioning swab from a rigid plastic tube, a suctioning thumb control, soft resilient tubular tip, and foam sleeve; the method comprising the steps of:
   heating the rigid plastic tube;
   bending the heated plastic tube to impart a bend in the plastic tube;
   mounting the soft tip on an end of said tube; and
   mounting the foam sleeve on the rigid plastic tube and soft tip without relative sliding friction motion therebetween such that the foam sleeve drops onto the rigid plastic tube;
   whereby said foam sleeve does not wipe solvent off the bond surface of the tube as it is moved onto the tube end, and said soft tip extends beyond said foam sleeve.

7. The method of claim 6 wherein heating said rigid plastic tube includes applying heat to one side of the rigid plastic tube, generally one-half the circumference of said tube.

8. The method of claim 6 wherein bending said rigid plastic tube includes bending said heated tube to the bent shape without having to maintain the desired bent shape until sufficiently cool.

9. The method of claim 6 further including the step of mounting the suctioning thumb control on one end of said rigid plastic tube.

10. The method of claim 6 wherein mounting the soft tip includes applying solvent thereon; and inserting said soft tip into said rigid plastic tube.

11. The method of claim 6 wherein mounting the foam sleeve on the rigid plastic tube and soft tip without relative sliding friction motion therebetween includes the steps of:

mounting the foam sleeve on a taped mandrel having a hollow center;

inserting the soft tip end of the tube into the hollow center of the mandrel;

restraining said foam sleeve relative to said rigid plastic tube; and extracting the mandrel from the foam sleeve whereby the foam sleeve is dropped onto the soft tip end of the tube without relative sliding friction motion.

* * * * *